(12) United States Patent
Hoffmann et al.

(10) Patent No.: US 8,702,794 B2
(45) Date of Patent: Apr. 22, 2014

(54) BACK LOADED IOL INSERTION CARTRIDGE

(75) Inventors: Laurent G. Hoffmann, Aliso Viejo, CA (US); David A. Ruddocks, Mission Viejo, CA (US); Mark C. Cole, Trabuco Canyon, CA (US); Daniel G. Brady, San Juan Capistrano, CA (US)

(73) Assignee: Abbott Medical Optics Inc., Santa Ana, CA (US)

(*) Notice: Subject to any disclaimer, the term of this patent is extended or adjusted under 35 U.S.C. 154(b) by 1120 days.

(21) Appl. No.: 12/111,028

(22) Filed: Apr. 28, 2008

(65) Prior Publication Data
US 2009/0270876 A1    Oct. 29, 2009

(51) Int. Cl.
*A61F 2/16* (2006.01)
*A61F 9/00* (2006.01)

(52) U.S. Cl.
USPC .......................................... 623/6.12; 606/107

(58) Field of Classification Search
USPC ......... 206/5.1; 606/107; 623/6.11–6.12, 6.18, 623/902, 905–907
See application file for complete search history.

(56) References Cited

U.S. PATENT DOCUMENTS

| | | | |
|---|---|---|---|
| 4,681,102 A | 7/1987 | Bartell | |
| 5,474,562 A | 12/1995 | Orchowski et al. | |
| 5,702,402 A | 12/1997 | Brady | |
| 5,947,976 A * | 9/1999 | Van Noy et al. | 606/107 |
| 6,010,510 A | 1/2000 | Brown et al. | |
| 6,371,960 B2 | 4/2002 | Heyman et al. | |
| 6,491,697 B1 | 12/2002 | Clark et al. | |
| 6,500,181 B1 * | 12/2002 | Portney | 606/107 |
| 6,558,395 B2 | 5/2003 | Hjertman et al. | |
| 6,733,507 B2 | 5/2004 | McNicholas et al. | |
| 7,156,854 B2 | 1/2007 | Brown et al. | |
| 7,156,855 B2 | 1/2007 | Oda | |
| D578,643 S | 10/2008 | Shumer et al. | |
| 7,458,976 B2 | 12/2008 | Peterson et al. | |
| 7,476,229 B2 | 1/2009 | Meyer | |
| 7,754,953 B2 | 7/2010 | Takegawa | |
| 2002/0193805 A1 | 12/2002 | Ott et al. | |
| 2006/0293694 A1 * | 12/2006 | Futamura | 606/107 |
| 2008/0097459 A1 | 4/2008 | Kammerlander et al. | |
| 2008/0114313 A1 | 5/2008 | Gomez et al. | |
| 2008/0255577 A1 | 10/2008 | Downer et al. | |
| 2008/0312661 A1 | 12/2008 | Downer et al. | |

(Continued)

FOREIGN PATENT DOCUMENTS

| | | |
|---|---|---|
| BE | 1016692 A3 | 4/2007 |
| EP | 1360944 B1 | 9/2007 |

(Continued)

*Primary Examiner* — Ashley Fishback
(74) *Attorney, Agent, or Firm* — Abbott Medical Optics Inc.

(57) ABSTRACT

A rear-loaded injector cartridge for an intraocular lens (IOL) having a proximal opening that provides a haptic slot. The haptic slot receives a leading haptic of an IOL loaded therein, and temporarily retains the leading haptic while the optic of the IOL is inserted into a holding area of the cartridge. As the optic passes by, the leading haptic folds over the top of the optic, on its anterior side. The length of the haptic retention slot is sufficient to maintain the leading haptic in its anteriorly folded position while the IOL remains in holding area, typically while the cartridge is mated with a handpiece of the injector. The cartridge also has a rear or proximal cut out which advantageously keys with a similarly-sized rail on the handpiece so that the cartridge cannot be inserted in the wrong way.

19 Claims, 6 Drawing Sheets

(56) References Cited

U.S. PATENT DOCUMENTS

| | | |
|---|---|---|
| 2009/0204123 A1 | 8/2009 | Downer |
| 2010/0217273 A1 | 8/2010 | Someya et al. |
| 2010/0228260 A1 | 9/2010 | Callahan et al. |
| 2010/0278261 A1 | 11/2010 | Chujoh et al. |
| 2012/0022549 A1 | 1/2012 | Someya et al. |
| 2012/0071887 A1 | 3/2012 | Ichinohe et al. |

FOREIGN PATENT DOCUMENTS

| | | |
|---|---|---|
| EP | 2161005 A1 | 3/2010 |
| EP | 1737393 B1 | 6/2010 |
| EP | 2123239131 | 3/2012 |
| JP | 2000005204 A | 1/2000 |
| JP | 4707016 B2 | 6/2011 |
| WO | 96/20662 | 7/1996 |
| WO | WO0187187 A1 | 11/2001 |
| WO | WO03024356 A2 | 3/2003 |
| WO | WO2005020853 A2 | 3/2005 |
| WO | WO2005070341 A1 | 8/2005 |
| WO | 2005/084588 A1 | 9/2005 |
| WO | WO2008014260 A1 | 1/2008 |
| WO | WO2008060869 A2 | 5/2008 |

* cited by examiner

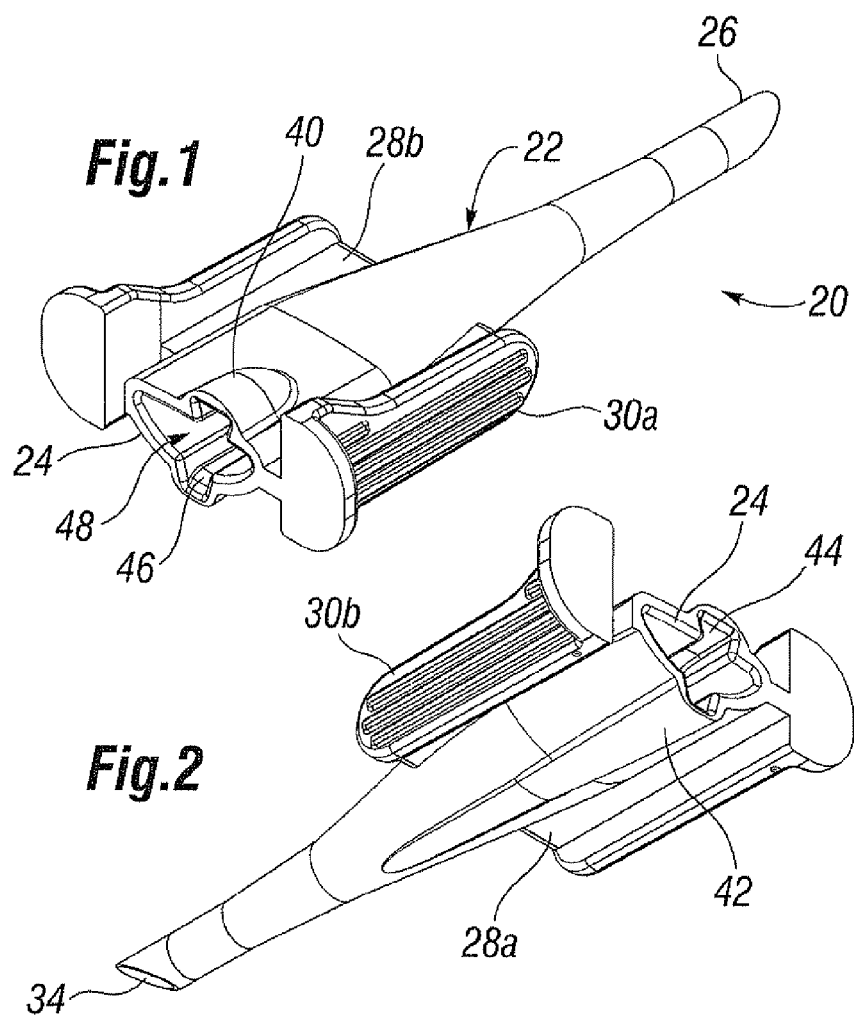
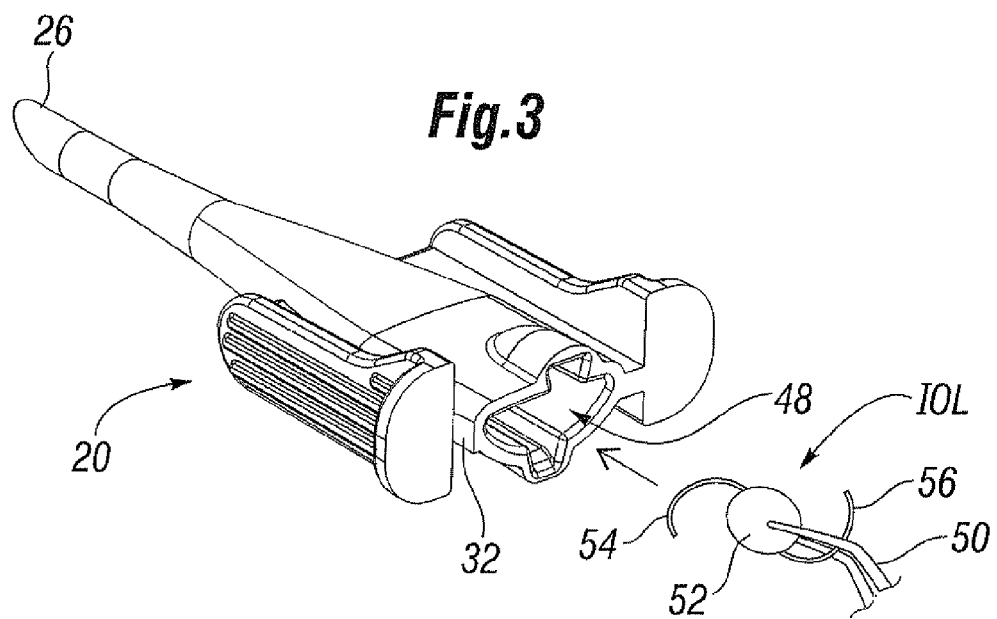

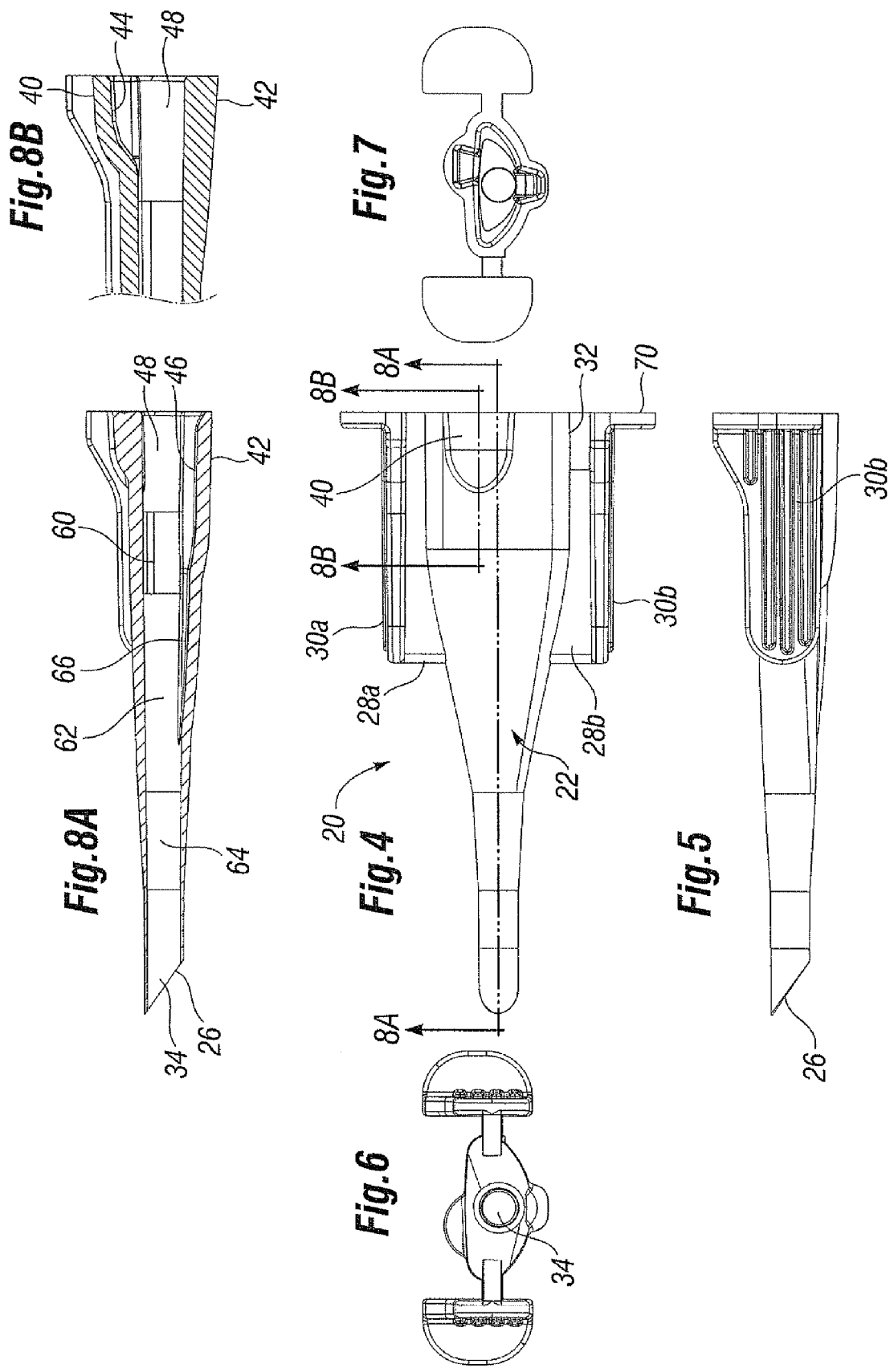

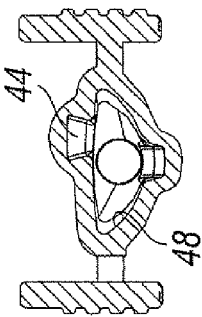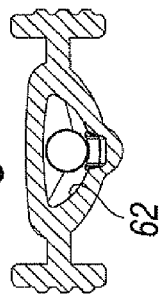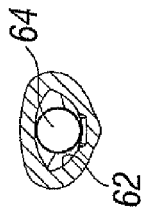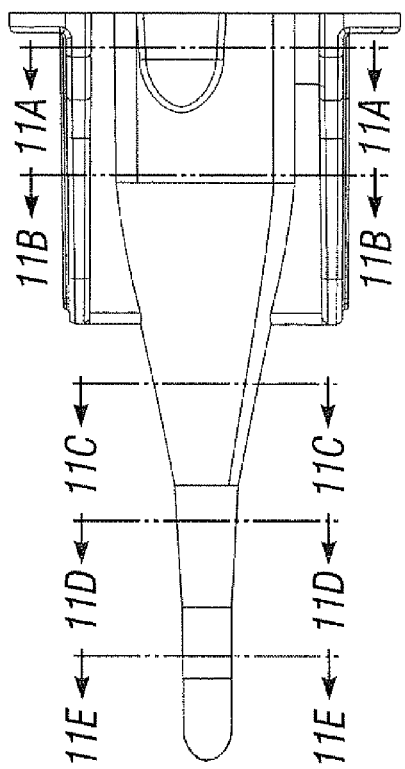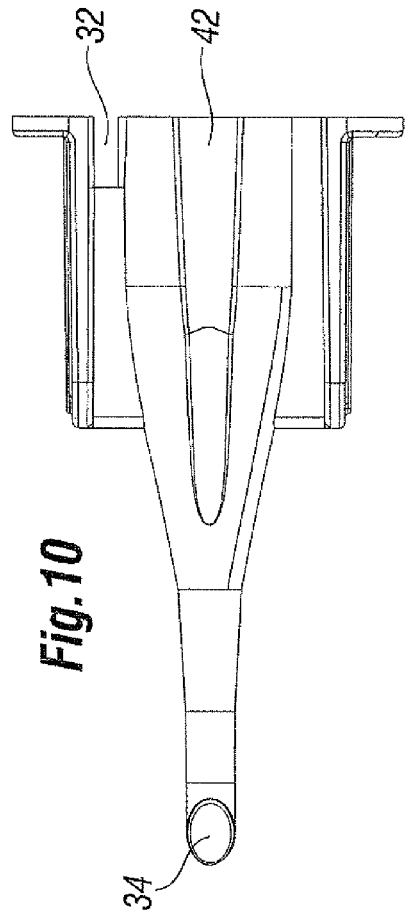

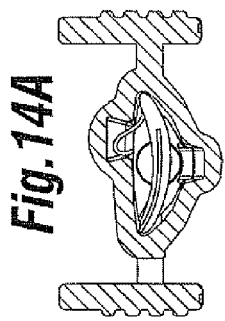
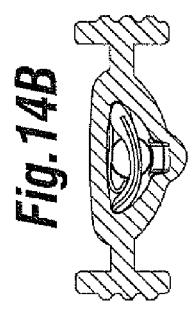
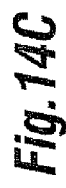
Fig.14A  Fig.14B  Fig.14C  Fig.14D  Fig.14E
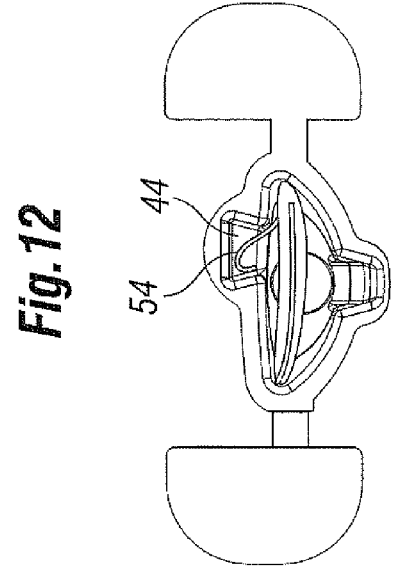
Fig.12
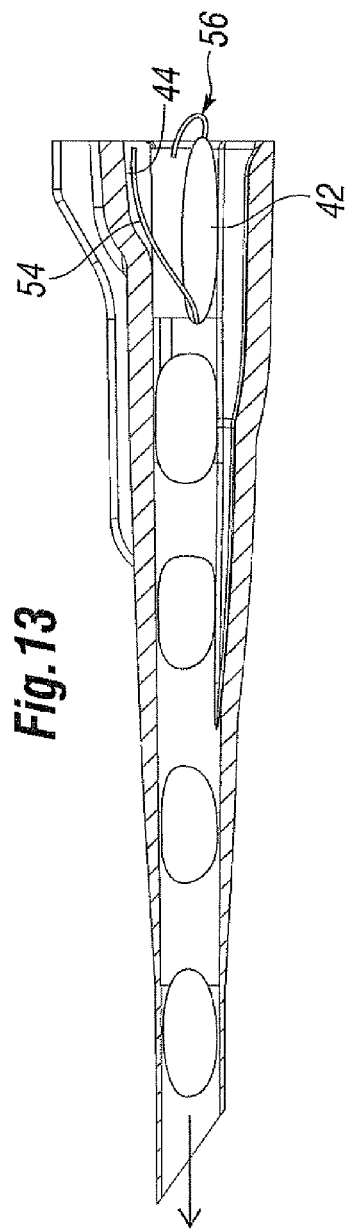
Fig.13

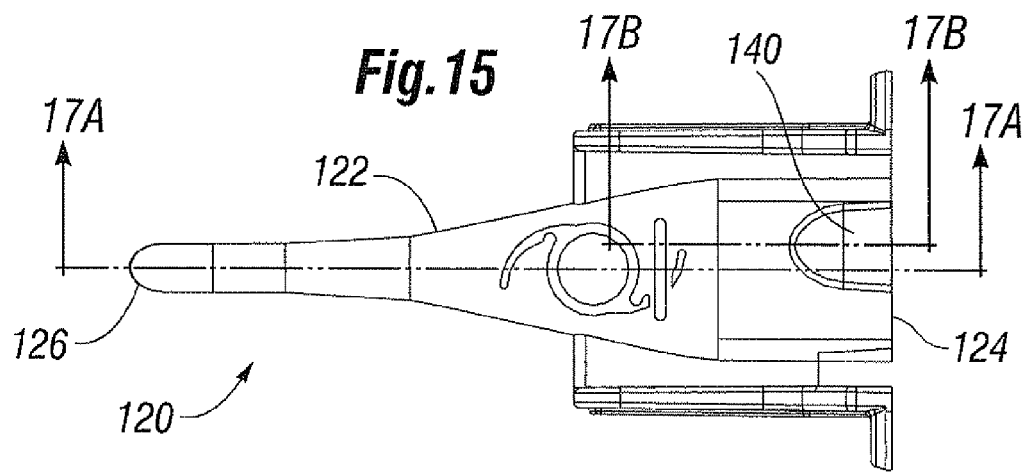
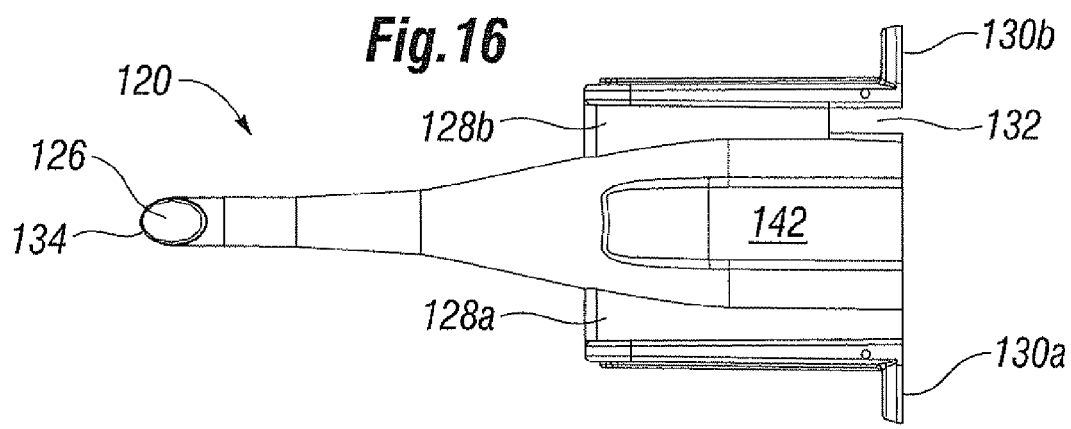
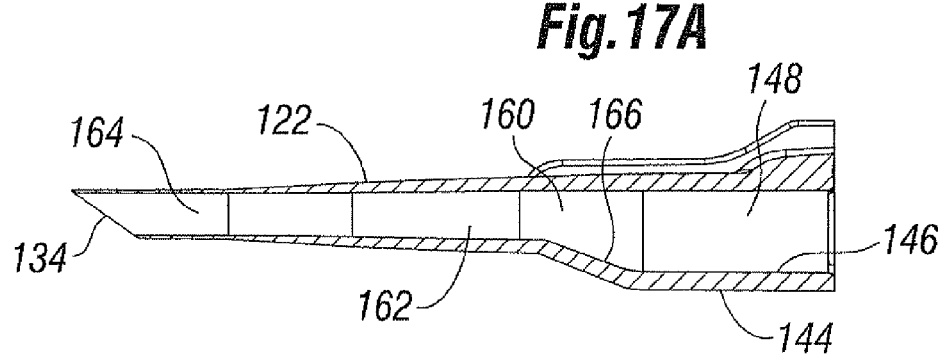
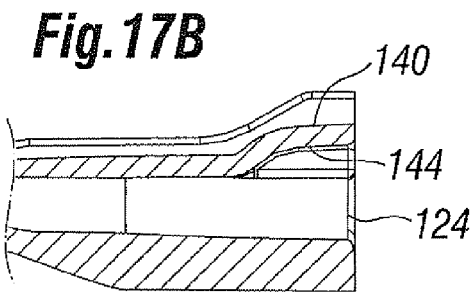

BACK LOADED IOL INSERTION CARTRIDGE

FIELD OF THE INVENTION

The present invention relates to devices, systems, and methods for delivering an intraocular lens (IOL) into an eye. More particularly, the invention relates to devices, systems, and methods for managing passage of an IOL through an injector cartridge.

BACKGROUND OF THE INVENTION

It is estimated that at least about 42% of Americans between the ages of 52 and 64 and 73% of Americans between the ages of 65 and 74 get cataracts. A cataract is a clouding of the eye's lens that impairs a person's vision and, if left untreated, causes blindness. As a result, each year approximately 1.4 million people in the United States alone undergo cataract surgery, whereby the clouded lens is removed and replaced with an intraocular lens (IOL) implant.

A typical IOL includes an optic or lens body for focusing light toward the retina of the eye. In addition, the IOL also includes one or more fixation members or haptics extending outward from the optic for securing and centering the IOL in the desired position within the chamber of the eye. The IOL is implanted directly into the eye through a small incision in a way that reduces trauma and expedites post-surgery healing. To fit through this small incision, modern IOLs are designed to be deformed, e.g., rolled, folded or the like, to a relatively small profile and then allowed to return to their original shape within the eye.

A useful technique for inserting an IOL into the eye includes use of an IOL injector or cartridge. Injectors for delivering IOLs into the eye typically employ a handpiece and a cartridge having a hollow insertion tube or cannula through which the folded IOL is passed using a pushrod. The cartridges are made of disposable materials, such as plastics, and remain in a sterile package until ready for coupling with the handpiece. Some injectors do without the cartridge, and may be reusable.

Conventional IOL cartridges include a load chamber connected to an injection tube. In many popular versions, such as in U.S. Pat. No. 4,681,102 to Bartell or U.S. Pat. No. 5,702,402 to Brady, the load chamber is formed by two hinged halves which receive the IOL, and which close to fold the IOL. A non-folding cartridge is seen in U.S. Pat. No. 5,474,562 to Orchowski in which forceps are used to insert the IOL into a proximal opening of the cartridge. The injection tube includes a small diameter distal tip that is insertable into the incision within the eye. After mating the cartridge with the handpiece (if a separate cartridge is used), the pushrod urges the IOL through the load chamber and the injection tube into the eye.

In general, the IOL is provided to the surgeon in packaging, such as a vial, plastic blister package, or other container for maintaining the IOL in a sterile condition. The IOL is removed from the packaging and placed on or in the load chamber prior to insertion into the patient's eye. The technique of removing the IOL from the packaging and transferring it to the load chamber is usually accomplished with a pair of forceps or similar device. The forceps simply place the IOL on or in the load chamber of the cartridge, or also fold the IOL to a reduced size for insertion into the eye.

Certain problems may be encountered during delivery of the IOL from the cartridge and into the eye of the subject. For instance, because the IOL is rolled inside the injection tube, the orientation of the optic and haptic portions may be difficult to control. In addition, problems may be encountered regarding engagement of the tip of the push-rod with the IOL, resulting in damage of optic, haptics, or both. For instance, the force required to push the IOL through the injection tube while it folds from contact with tapering walls may cause the rod to slip under or over the IOL, or to damage the optic.

In view of the above, there is a need for a cartridge that more effectively receives and manages passage of an IOL therethrough.

SUMMARY OF THE INVENTION

The present invention solves a number of issues with previous intraocular lens cartridges by including structure to managing passage of an intraocular lens therethrough, and also having a feature that enables registration with a handpiece in only one orientation.

In accordance with one aspect, the present invention provides a method of controlling passage of an intraocular lens through an injector cartridge. An exemplary injector cartridge has a proximal opening sized to receive an intraocular lens, a hollow interior extending longitudinally from the proximal opening to a distal insertion tip, and a holding area within the hollow interior spaced from the proximal opening. The proximal opening is interrupted by a peripheral slot that extends from the proximal opening in a distal direction and terminates prior to reaching the holding area. Preferably, the peripheral slot extends distally from the proximal opening a distance of between 3.5-9.3 mm. The method also includes providing an intraocular lens having an optic, a leading haptic, and a trailing haptic, and inserting the intraocular lens into the cartridge through the proximal opening by registering the leading haptic with the peripheral slot and displacing the optic of the intraocular lens past the slot and into the holding area. In doing so, the leading haptic is guided by the peripheral slot and deforms so as to be located across one face of the optic. The intraocular lens is then urged from the holding area through the hollow interior and out of the distal insertion tip. The hollow interior is sized to maintain the leading haptic located across one face of the optic until the intraocular lens emerges from the distal insertion tip.

In accordance with the aforementioned method, the step of inserting the intraocular lens is accomplished using forceps. Also, the cartridge with the intraocular lens in the holding area is desirably positioned within a handpiece having a pushrod, wherein the step of urging the intraocular lens through the hollow interior of the cartridge comprises extending the pushrod through the cartridge and pushing the intraocular lens from the holding area through the remainder of the hollow interior. The cartridge may include an asymmetrically located cutout, wherein the method includes registering the cutout with corresponding structure on the handpiece to ensure proper orientation. In one embodiment, the optic of the intraocular lens has a diameter smaller than a width of the proximal opening and larger than the width of the holding area such that the optic deforms as it is inserted from the proximal opening to the holding area. The cartridge hollow interior gradually narrows in a distal direction and the intraocular lens undergoes folding into a generally tubular shape as it passes distally therethrough, wherein the dimensions of the holding area are such that the intraocular lens undergoes a majority of the deformation of folding by the time it reaches the holding area. In one embodiment, the holding area has a horizontal width of between 2.5-4.5 mm, and the intraocular lens optic has a diameter of at least 5.0 mm.

Another aspect of the present invention is an intraocular lens injector cartridge for controlling passage of an intraocular lens having an optic, a leading haptic, and a trailing haptic. The cartridge has a cartridge body with a proximal opening sized to receive an intraocular lens and a larger width perpendicular to a central vertical plane than its height within the vertical plane. A hollow interior of the cartridge extends longitudinally from the proximal opening to a distal insertion tip, and a holding area within the hollow interior is spaced from the proximal opening. A peripheral slot interrupts the proximal opening and extends from the proximal opening in a distal direction, terminating prior to reaching the holding area. The peripheral slot is horizontally offset so that the proximal opening is asymmetric about the central vertical plane. Preferably, the peripheral slot extends distally from the proximal opening a distance of between 3.5-9.3 mm.

Desirably, the cartridge body further defines an outwardly bulged canopy over the peripheral slot. In a preferred embodiment, the optic of the intraocular lens has a diameter, the horizontal width of the proximal opening is larger than the diameter of the optic and the horizontal width of the holding area is smaller than the diameter of the optic, such that the optic deforms as it is inserted from the proximal opening to the holding area. In a particular embodiment, the holding area has a horizontal width of between 2.5-4.5 mm, and the intraocular lens optic has a diameter of at least 5.0 mm. The cartridge may also include an asymmetrically located cutout, such as a cutout positioned between one of a pair of finger grips extending horizontally from the cartridge body and the cartridge body.

A still further aspect of the present invention is an intraocular lens injector system for controlling delivery of an intraocular lens having an optic, a leading haptic, and a trailing haptic, comprising an injector cartridge body and a handpiece having a pushrod. The cartridge body has a proximal opening sized to receive an intraocular lens and a larger width perpendicular to a central vertical plane than its height within the vertical plane. A hollow interior extends longitudinally from the proximal opening to a distal insertion tip. A holding area within the hollow interior is spaced from the proximal opening. A peripheral slot interrupts the proximal opening and extends from the proximal opening in a distal direction, terminating prior to reaching the holding area. The peripheral slot horizontally offset such that the proximal opening is asymmetric about the central vertical plane. The handpiece provides a cradle for receiving the cartridge, wherein the pushrod is aligned in the handpiece to pass longitudinally through the hollow interior of the cartridge and urge an intraocular lens therethrough.

In a preferred embodiment the cartridge further includes an asymmetrically located cutout, and the handpiece cradle includes structure for mating with the cutout such that the cartridge can only be received in the cradle in one orientation. Preferably, the cartridge further includes a pair of finger grips extending horizontally from the cartridge body, wherein the asymmetrically located cutout is positioned between one of the finger grips and the cartridge body. In accordance with one aspect, the hollow interior of the cartridge defines an upper wall and the lower wall along the central vertical plane, wherein the upper wall is generally horizontal, and the lower wall is angled and gradually converges toward the upper wall in a distal direction. In particular, the pushrod translates generally longitudinally through the cartridge hollow interior and contacts the angled lower wall midway therethrough. For instance, the lower wall may form an angle of greater than 0° and up to about 30° with the horizontal, preferably about 20°.

BRIEF DESCRIPTION OF THE DRAWINGS

Embodiments of the present invention will be better understood from the following detailed description when read in conjunction with the accompanying drawings. Such embodiments, which are for illustrative purposes only, depict the novel and non-obvious aspects of the invention. The drawings include the following figures, with like numerals generally indicating like parts:

FIGS. 1 and 2 are perspective top and bottom views, respectively, of an exemplary intraocular lens (IOL) cartridge of the present invention;

FIG. 3 is a top perspective view of the exemplary IOL cartridge from a different angle than FIG. 1 and schematically illustrating an IOL held by forceps just prior to introduction into the cartridge;

FIGS. 4-7 are various plan and elevational views of the exemplary IOL cartridge of the present invention;

FIGS. 8A and 8B are longitudinal sectional views through the exemplary IOL cartridge taken along lines 8A-8A and 8B-8B of FIG. 4;

FIGS. 9 and 10 are top and bottom plan views, respectively, of the exemplary IOL cartridge;

FIGS. 11A-11E are transverse sectional views through the exemplary IOL cartridge taken along corresponding section lines shown in FIG. 9;

FIG. 12 is a rear plan view of the exemplary IOL cartridge showing an IOL in an initial load position therein;

FIG. 13 is a longitudinal sectional view as in FIG. 8A and showing the IOL in several positions therethrough, including a load position with a leading haptic captured in an upper slot;

FIGS. 14A-14E are transverse sectional views through the exemplary IOL cartridge taken at the same locations as FIGS. 11A-11E and showing an IOL at those locations as it passes through the cartridge;

FIGS. 15 and 16 are top and bottom plan views, respectively, of an alternative exemplary IOL cartridge;

FIGS. 17A and 17B are vertical sectional views through the alternative IOL cartridge taken along corresponding section lines shown in FIG. 15;

DETAILED DESCRIPTION OF THE PREFERRED EMBODIMENTS

Figure 19:
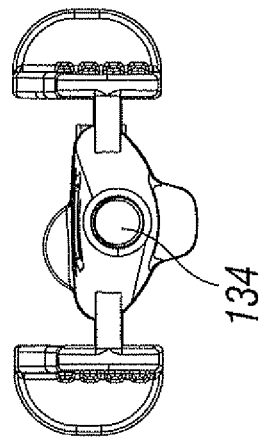
FIG. 19 is a horizontal sectional view through the alternative IOL cartridge looking upward along section line 19-19 of FIG. 18.
Figure 18:
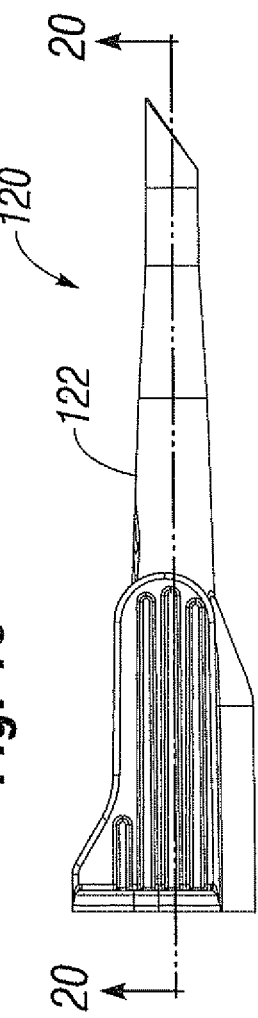
FIG. 18 is an elevational view of the alternative IOL cartridge of FIG. 15.
Figure 21:
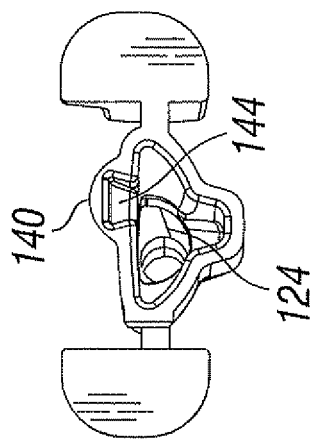
FIG. 21 is an elevational view at a slight angle of the proximal end of the alternative IOL cartridge of FIG. 18.
Figure 20:
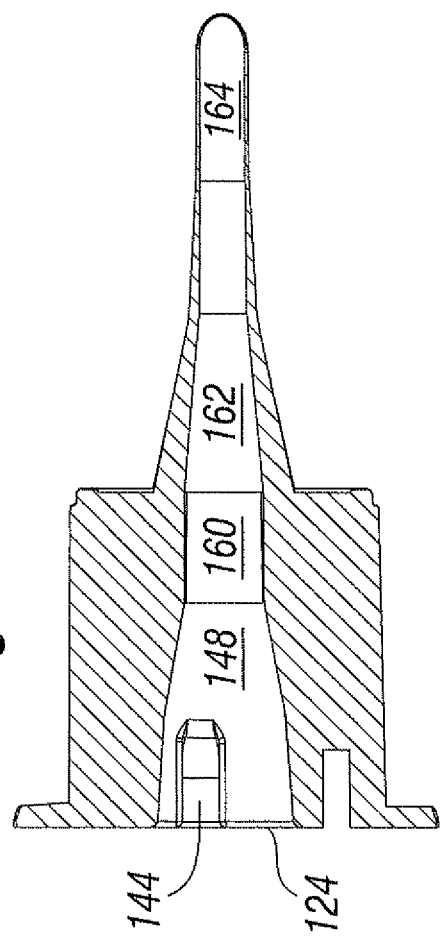
FIG. 20 is an elevational view of the distal end of the alternative IOL cartridge of FIG. 18.

Embodiments of the present invention provide a rear- or back-loaded intraocular lens cartridge for use in an IOL injector. As explained above, some injectors combine the features of the cartridge and handpiece in one device, and it should be understood that the description herein applies to both separate and such built-in cartridges.

Referring to FIGS. 1-3, which shows an IOL cartridge 20 according to an embodiment of the present invention from several perspectives, a cartridge 20 includes a main body 22 extending longitudinally from a proximal opening 24 to a distal tip 26. A pair of webs 28a, 28b project transversely outward from opposite sides of the main body 22 and terminates in a generally vertically-oriented finger grip 30a, 30b. The finger grips 30 are substantially identical and the left web 28b is shorter than the right web 28a, and specifically does not extend as far as the proximal opening 24. As a result, a rearwardly-opening longitudinal cutout 32 exists on the left side of the cartridge 20 between the left finger grip 30b and the main body 22, seen best in FIG. 3. As will be clearer below, the cutout 32 is asymmetrically located about a vertical center line of the cartridge 20 and may be configured to mate with a similar male feature on an associated handpiece to ensure proper orientation of the cartridge therein. It will be appreciated that the geometry of the webs 28a, 28b and the finger grips 30a, 30b may be modified from the illustrated embodiment to suit the requirements or preferences of a particular design. For example, the webs 28a, 28b may be made substantially identical so that the webs 28a, 28b have the same extent.

The main body 22 of the cartridge 20 defines a lumen or hollow interior extending longitudinally from the proximal opening 24 to a distal opening 34 at the distal tip 26. At the proximal opening 24, the main body 22 has a somewhat flattened oval shape interrupted by an upper canopy 40 and a lower canopy 42 disposed adjacent the opening 24. In particular, the periphery of the proximal opening 24 may define a modified oval that generally has a larger horizontal width than its vertical height. In certain embodiments, for example as seen in FIG. 7, the proximal opening 24 is somewhat bowl-shaped with a convex lower wall that has a smaller radius than the curvature of the slightly convex upper wall. The perimeter of the proximal opening 24 may have other shapes suitable for receiving an IOL including, but not limited to, rectangular, circular, oval, and the like. In some embodiments, the perimeter of the proximal opening 24 is defined by a shape that includes corner and/or smooth curves free of inflections (e.g., without a change in curvature of a curve from concave to convex or conversely).

The outwardly bulged upper canopy 40 defines therein an upper slot or groove 44 extending in a distal direction, while the outwardly bulged lower canopy 42 defines a lower groove 46, also extending distally from the opening 24. The periphery of the proximal opening 24 is thus interrupted twice, once by the upper slot 44 and again by the lower groove 46—thus defining peripheral openings adjacent the opening 24. The hollow interior of the main body 22 just inside the proximal opening 24 is termed a load chamber 48, as it is where the IOL is first loaded into the cartridge. With reference to FIGS. 3 and 7, the load chamber 48, the upper canopy 40, and the lower canopy 42 together form a complex opening that is defined by the proximal opening 24 and adjacent openings formed by the upper and lower canopies 40, 42 that are each offset from the proximal opening 24. The complex opening may be disposed in a single plane, or along a curved or more complex surface.

FIG. 3 illustrates an IOL held by tongs of forceps 50. This type of IOL includes a central disc-shaped optic 52, a leading haptic 54, and a trailing haptic 56. Typically, the optic 52 has opposed convex faces, although the present invention is not limited to handling any particular type of IOL. The haptics 54, 56 are shown as thin arcuate members extending outward from opposite edges of the optic 52, and generally in the plane of the optic. The haptics 54, 56 curve in the same direction, in this case a counter-clockwise direction looking down on the IOL.

Other arrangements of haptics around the optic of IOLs are known, and the present invention is intended to provide a cartridge solution for the illustrated haptic design as well as others. In particular, IOLs having leading and trailing haptics often encounter difficulties passing through the cartridge with regard to orientation or positioning of the haptics. If one or both of haptics becomes misaligned or otherwise mispositioned within the cartridge, the IOL may exit the distal tip of the cartridge in a manner that requires further positioning within the eye. Desirably, the surgeon controls delivery of the IOL in such a way that it exits the cartridge in the proper orientation to minimize any further need for repositioning.

With reference still to FIGS. 1-3, and also to the detailed views of FIGS. 4-8, additional features of the exemplary cartridge 20 will be described. FIG. 4 illustrates the cartridge 20 from above such that the offset transverse position of the upper canopy 40 is evident. The section line 8A-8A extends along a longitudinal center line of the cartridge 20. The cartridge 20 generally exhibits symmetry across a vertical plane through this center line, except for the position of the upper canopy 40 and the aforementioned cutout 32.

FIG. 8A shows an exemplary arrangement of the contours of the walls of the main body 22, and in particular its hollow interior, along the vertical center line. In the illustrated embodiment, the hollow interior of the main body 22 defines the load chamber 48. Above and below the load chamber 48 are chambers defined by the grooves 44, 46. Adjacent thereto is a holding area 60 leading to a folding channel 62 that may be gradually tapered. In some embodiments, at least one of the grooves 44, 46 may border at least a portion of the holding area 60 or even the folding channel 62. Adjacent the folding channel 62 is a delivery channel 64 that extends to the distal opening 34. The upper wall of the hollow interior of the cartridge main body 22 extends generally parallel to the horizontal, while the lower and side walls gradually taper inward in a distal direction. The lower groove 46 within the lower canopy 42 may form a slight angle with the horizontal so as to create a gradually narrowing ramp 66 in the distal direction. The ramp 66 extends into the folding channel 62, and is adjacent thereto. Other geometries of the hollow interior of the cartridge main body 22 are consistent with embodiments of the IOL cartridge 20.

In certain embodiments, the entire lower wall of cartridge hollow interior, encompassing the ramp 66, is generally angled and gradually converges toward the upper wall in a distal direction. In the illustrated embodiment, the lower wall forms a small angle with the horizontal; however, this angle may be from 0 degrees to about 30 degrees with the horizontal, and is generally between about 5 degrees and about 20 degrees. In other embodiments, the upper wall of the interior additionally or alternatively is generally angled and gradually converges toward the upper wall in a distal direction.

The cartridge is generally configured to mate with a handpiece (not shown) having a pushrod which translates generally longitudinally through the cartridge hollow interior and contacts the angled lower wall midway therethrough. In some embodiments, the pushrod has a forked distal end that helps capture the proximal edge of the optic 52. Additionally or alternatively, the distal end of the pushrod may have a lower tip that is configured to insert into the lower groove 46, for example, to help prevent the pushrod tip from riding on top of or underneath the optic 52 when it is disposed within the cartridge 20.

The slot 44 that interrupts the proximal opening 24 generally extends in a distal direction from the opening 24 and has a length that is generally between about 1 mm and 10 mm, preferably between 2 mm and 6 mm. In the illustrated embodiment, the slot 44 advantageously terminates prior to reaching the holding area 60. This arrangement can help ensure proper management of a leading haptic as the IOL passes through the cartridge, as will be explained below.

In another significant change from cartridges of the prior art, the intraocular lens undergoes folding into a generally tubular shape as it passes distally therethrough, and the dimensions of the holding area 60 are such that the intraocular lens undergoes at least some, and in some embodiments a majority, of the deformation of folding by the time it reaches the holding area. For instance, the holding area 60 has a horizontal width of between 2.5-4.5 mm, and the intraocular lens optic has a diameter of at least 5.0 mm. To define this feature, the optic of the IOL typically folds or rolls into a generally tubular shape, and the majority of deformation of folding may be measured by examining the geometry of the folded optic. In other words, the optic begins generally flat, and may deform into a rolled circle wherein the side edges that fold up and touch are oriented 180° from their relaxed orientation. In this simple example, a majority of fold deformation has occurred when the side edges have folded 90° or more. It should be understood final configuration of the optic may be more or less circular, depending on the size of the optic relative to the size of the cartridge lumen.

Each of the finger grips 30a, 30b includes a plurality of longitudinal ribs to help facilitate handling of the cartridge. A pair of proximal flanges 70 project outward from the finger grips 30 and define structural features that function as a tactile reference for the proximal end of the cartridge 24 when the cartridge is held by the finger grips 30.

Use of the exemplary cartridge 20 of the present invention will now be described.

As schematically indicated in FIG. 3, the process begins by inserting the intraocular lens (IOL) into the proximal opening 24 of the cartridge. Often, a fluid or viscoelastic medium is first introduced into the hollow interior of the cartridge through the proximal opening 24 to facilitate passage of the IOL therethrough. Typical intraocular lenses have optic diameters of at least 5.0 mm, and the proximal opening 24 is sized to easily receive the intraocular lens. For example, the proximal opening 24 has a horizontal width of at least 6 mm such that the IOL can be inserted therethrough in a horizontal orientation without touching the opening.

As the IOL enters the proximal opening 24, the operator, using forceps 50 or the like, registers the leading haptic 54 with the upper slot 44. Further passage of the IOL into the load chamber 48 causes the leading haptic 54, constrained by the peripheral slot, to deform across one face of the optic, typically the anterior face, as seen in FIGS. 12, 13, and 14A. The ramp configuration of the inner wall of the canopy 40 facilitates a gradual folding of the leading haptic 54 in this manner. Additionally, as seen in FIGS. 7 and 11A, the slot 44 is generally trapezoidal in cross-section section, with a larger upper dimension. This helps trap the filament-like haptic 54 therein, and ensures that it remains in the slot 44 as the optic 52 passes there under.

The operator passes the IOL through the load chamber 48 and into the holding area 60, as seen in FIGS. 13 and 14B. As mentioned above, the holding area 60 has a horizontal width that is less than the diameter of the optic 52. This causes the lateral edges of the optic 52 to contact the sides of the holding area 60. Because of the bowl-shape of the lead-in load chamber 48 and holding area 60, the lateral edges of the optic 52 fold or curl upward relative to the center. The lower groove 46 helps in this folding process by providing relief into which the central area of the optic may deform. Desirably, the holding area 60 has a substantially constant horizontal width along a length of at least 4 mm, preferably between 4-8 mm, and most preferably approximately the diameter of the particular optic 52. For example, a common optic diameter is 6 mm, so the holding area 60 also has a substantially constant horizontal width of at least 6 mm. As the optic 52 passes through the cartridge 20, therefore, the hollow interior first narrows from the proximal opening 24 to the holding area 60, curling the optic, then remains constant in the holding area for the optic to rest, and then narrows further distally to the distal tip 26. More generally, the holding area 60 has a constant cross-section along its length when the lower groove 46 is excluded.

One benefit of the reduced size holding chamber is that a majority of IOL folding occurs therein and thus less of the push force applied by the pushrod to the lens is needed for subsequent folding. In an example where the holding area 60 has a horizontal width of 50-75% of the diameter of optic, the optic effectively curls into its delivery shape by the time it reaches the holding area. This helps reduce damage to the optic or slippage of the rod past the IOL. One function of the substantially cylindrical and constant cross-section holding area 60 is to provide a sanctuary of sorts for the lens to remain in a stable position between proximal and distal funnels within the cartridge.

Furthermore, the slot 44 terminates prior to reaching the holding area 60 which reduces the vertical dimension above the optic 52. By this time, the leading haptic 54 is trapped above the optic 52 and remains so because of the close spacing there above. The trailing haptic 56 presents less of the problem to the operator, as it resiliently straightens out through the cartridge and resumes its original shape once the IOL exits the distal tip 26.

At this point, the operator mates the cartridge 20, having the IOL within the holding area 60, with the handpiece of the injector. As mentioned above, the asymmetrically offset cutout 32 registers with a similar male feature on the handpiece to ensure proper orientation of the cartridge therein.

The operator then urges the IOL from the holding area 60 through the hollow interior of the cartridge 20 and out of the distal insertion tip 26, as seen in FIGS. 13 and 14C-14E. The hollow interior gradually narrows and further reduces the profile of the IOL for passage into an incision in the eye. The tapered folding channel 62 provides a transition from the bowl shapes of the load chamber 48 and holding area 60 to the circular cross-sections of the delivery channel 64 and distal opening 34. Moreover, the hollow interior is sized to maintain the leading haptic 54 located across one face of the optic 52 until the IOL emerges from the distal insertion tip. In this manner, the operator maintains maximum control of the IOL and the leading haptic 54.

With reference now to FIGS. 15-21, an alternative exemplary IOL cartridge 120 similar to the first-described cartridge is shown. As before, the cartridge 120 includes a main body 122 extending longitudinally from a proximal opening 124 to a distal tip 126. Each of a pair of webs 128a, 128b projects transversely outward from opposite sides of the main body 122 and terminates in a generally vertically-oriented finger grip 130a, 130b. A rearwardly-opening longitudinal cutout 132 exists on the left side of the cartridge 120 between the left finger grip 130b and the main body 122.

The main body 122 of the cartridge 120 defines a lumen or hollow interior extending longitudinally from the proximal opening 124 to a distal opening 134 at the distal tip 126. At the proximal opening 124, the main body 122 has a somewhat flattened oval shape interrupted by an upper canopy 140 and a lower canopy 142. In particular, the proximal opening 124 may define a modified oval having a larger horizontal width than its vertical height. Alternatively, the proximal opening 124 may have any of the shapes discussed above with regard to the proximal opening 24. The outwardly bulged upper canopy 140 defines therein an upper slot 144 extending in a distal direction, while the outwardly bulged lower canopy 142 defines a lower groove 146, also extending distally from the opening 124. The periphery of the proximal opening 124 is thus interrupted twice, once by the upper slot 144 and again by the lower groove 146—which therefore define peripheral slots.

FIGS. 17A and 17B show the longitudinal vertical contours of the walls of the main body 122, and FIG. 19 shows the horizontal mid-plane contours. The hollow interior begins with a load chamber 148 just inside the proximal opening 124 where the IOL is first loaded into the cartridge. Adjacent thereto is a holding area 160 leading to a gradually tapering folding channel 162, and finally to a delivery channel 164 that extends to the distal opening 134. The bounds of the holding area 160 are best seen in FIG. 19. The upper wall of the hollow interior of the cartridge main body 122 extends generally parallel to the horizontal, while the lower and side walls taper inward in a distal direction. The load chamber 148, the upper canopy 140, and the lower canopy 142 together form a complex opening that is defined by the proximal opening 124 and adjacent proximal openings formed by the upper and lower canopies 140, 142 that are each offset from the proximal opening 124. The complex opening may be disposed in a single plane, or along a curved or more complex surface.

The lower groove 146 within the lower canopy 142 may define a portion of the load chamber 140. The lower groove 146 extends generally horizontally until reaching a ramp 166 that tapers inward in the distal direction, generally at an angle of between about 15-30°, and preferably 20°. The ramp 166 extends into the folding channel 162, and may form a part thereof.

In contrast with the first embodiment, the lower wall of cartridge hollow interior is generally horizontal until the ramp 166, where it converges relatively quickly toward the upper wall. Ultimately, the cartridge mates with a handpiece (not shown) having a pushrod which translates generally longitudinally through the cartridge hollow interior and contacts the ramp 166 midway therealong. Again, the pushrod may have a forked distal end that helps capture the proximal edge of the optic.

The slot 144 that interrupts the proximal opening 124 desirably extends in a distal direction and terminates prior to reaching the holding area 160. For instance, the slot 144 in the illustrated embodiment extends distally from the proximal opening 124 a distance of about 4 mm, while the holding area 160 commences at a distance of about 9 mm from the proximal opening 124. This arrangement may help ensure proper management of a leading haptic as the IOL passes through the cartridge, as explained above.

As before, the intraocular lens undergoes folding into a generally tubular shape as it passes distally therethrough, and the dimensions of the holding area 160 are such that the intraocular lens undergoes at least some deformation of folding by the time it reaches the holding area. For instance, the holding area 160 has a horizontal width of between 2.5-4.5 mm, and the intraocular lens optic has a diameter of at least 5.0 mm.

Advantageously, the holding area 160 has a substantially constant horizontal width along a length of at least 4 mm, preferably between 4-8 mm, and most preferably approximately the diameter of the particular optic. For example, a common optic diameter is 6 mm, so the holding area 160 also has a substantially constant horizontal width of at least 6 mm. More generally, the holding area 160 has a constant cross-section along its length (e.g., when the lower groove 146 is excluded).

The present invention provides a cartridge where the horizontal width of the opening into the load chamber 148 is greater than or equal to the optic lens diameter, while the width of the holding area 160 is less than the lens diameter, thus compressing the lens at least slightly. As the optic passes through the cartridge 120, therefore, the hollow interior first narrows from the proximal opening 124 to the holding area 160, curling the optic, then remains constant in the holding area providing a place for the optic to pause, and then narrows further distally to the distal tip 126. This can best be seen in FIG. 20. The lens remains slightly compressed in the holding area 160 while in the cartridge 120 until the time of insertion into the eye. One advantages of this is to maintain a stable and repeatable lens configuration just prior to insert, and subsequently a smooth deformation of the lens upon insertion during surgery.

The above description represents the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that described above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An intraocular lens injector cartridge for controlling passage of an intraocular lens having an optic, a leading haptic, and a trailing haptic, comprising:
   an injector cartridge body having a distal end and a proximal opening, wherein the proximal opening is sized to receive an intraocular lens and has a width perpendicular to a central vertical plane that is greater than its height within the vertical plane, wherein the central vertical plane extends along a longitudinal axis of the injector cartridge body, a hollow interior extending longitudinally from the proximal opening to a distal insertion tip, and a holding area within the hollow interior spaced from and in between the proximal opening and a delivery channel that extends to the distal end, the proximal opening being interrupted by a first peripheral slot that extends from the proximal opening in a distal direction and terminates prior to reaching the holding area, the first peripheral slot being horizontally offset such that the proximal opening is asymmetric about the central vertical plane, and the proximal opening being interrupted by a second peripheral slot that extends from the proximal opening in a distal direction and terminates within the holding area or a folding area between the holding area and the distal end, the second peripheral slot being substantially symmetrical about the central vertical plane.

2. The cartridge of claim 1, wherein the first peripheral slot extends distally from the proximal opening a distance of between 3.5 and 9.3 mm.

3. The cartridge of claim 1, wherein the cartridge body further defines an outwardly bulged canopy over the first peripheral slot.

4. The cartridge of claim 1, wherein the horizontal width of the proximal opening is larger than the diameter of an optic of an intraocular lens and the horizontal width of the holding area is smaller than the diameter of the optic, such that the optic deforms as it is inserted from the proximal opening to the holding area.

5. The cartridge of claim 4, wherein the holding area has a horizontal width of between 2.5 and 4.5 mm.

6. The cartridge of claim 4, wherein the holding area has a substantially constant horizontal width along a length of at least 2 mm.

7. The cartridge of claim 1, wherein the cartridge further includes an asymmetrically located cutout.

8. The cartridge of claim 7, wherein the cartridge further includes a pair of finger grips extending horizontally from the cartridge body, wherein the asymmetrically located cutout is positioned between one of the finger grips and the cartridge body.

9. An intraocular lens injector system for controlling delivery of an intraocular lens having an optic, a leading haptic, and a trailing haptic, comprising:

an injector cartridge body having a distal end and a proximal opening, wherein the proximal opening is sized to receive an intraocular lens and has a width perpendicular to a central vertical plane that is greater than its height within the vertical plane, wherein the central vertical plane extends along a longitudinal axis of the injector cartridge body, a hollow interior extending longitudinally from the proximal opening to a distal insertion tip, and a holding area within the hollow interior spaced from and in between the proximal opening and a delivery channel that extends to the distal end, the proximal opening being interrupted by a first peripheral slot that extends from the proximal opening in a distal direction and terminates prior to reaching the holding area, the first peripheral slot being horizontally offset such that the proximal opening is asymmetric about the central vertical plane, and the proximal opening being interrupted by a second peripheral slot that extends from the proximal opening in a distal direction and terminates within the holding area or a folding area between the holding area and the distal end, the second peripheral slot being substantially symmetrical about the central vertical plane; and a handpiece having a pushrod, the handpiece piece having a cradle for receiving the cartridge, wherein the pushrod is aligned in the handpiece to pass longitudinally through the hollow interior of the cartridge and urge an intraocular lens therethrough.

10. The system of claim 9, wherein the first peripheral slot extends distally from the proximal opening a distance of between 3.5 and 9.3 mm.

11. The system of claim 9, wherein the cartridge further includes an asymmetrically located cutout and the handpiece cradle includes structure for mating with the cutout such that the cartridge can only be received in the cradle in one orientation.

12. The system of claim 11, wherein the cartridge further includes a pair of finger grips extending horizontally from the cartridge body, wherein the asymmetrically located cutout is positioned between one of the finger grips and the cartridge body.

13. The system of claim 9, wherein the hollow interior of the cartridge defines an upper wall and a lower wall along the central vertical plane, wherein the upper wall is generally horizontal, and the lower wall is angled and gradually converges toward the upper wall in a distal direction.

14. The system of claim 13, wherein the pushrod translates generally longitudinally through the cartridge hollow interior and contacts the angled lower wall midway therethrough.

15. The system of claim 14, wherein the lower wall forms an angle of greater than 0° and up to about 30° with a horizontal plane of the injector cartridge body.

16. The system of claim 9, wherein the horizontal width of the proximal opening is larger than the diameter of an optic of an intraocular lens and the horizontal width of the holding area is smaller than the diameter of the optic, such that the optic deforms as it is inserted from the proximal opening to the holding area.

17. The system of claim 16, wherein the holding area has a horizontal width of between 2.5 and 4.5 mm.

18. The system of claim 16, wherein the holding area has a substantially constant horizontal width along a length of at least 2 mm.

19. The system of claim 16, further comprising an intraocular lens, the intraocular lens comprising an optic with a diameter that is greater than the opening width perpendicular to the central vertical plane and less than a horizontal width of the holding area, the horizontal width of the holding area being constant along a length of at least 2 mm.

* * * * *